United States Patent [19]

Mita et al.

[11] Patent Number: 4,801,732
[45] Date of Patent: Jan. 31, 1989

[54] PREPARATION PROCESS OF α-L-ASPARTYL-L-PHENYLALANINE METHYL ESTER

[75] Inventors: Ryuichi Mita, Kawasaki; Takeshi Oura, Zushi; Chojiro Higuchi, Kamakura; Toshio Katoh, Kawasaki; Akihiro Yamaguchi, Kamakura, all of Japan

[73] Assignee: Mitsui Toatsu Chemicals, Incorporated, Tokyo, Japan

[21] Appl. No.: 171,134

[22] Filed: Mar. 22, 1988

Related U.S. Application Data

[63] Continuation of Ser. No. 63,736, Jun. 17, 1987, abandoned, which is a continuation of Ser. No. 809,800, Dec. 17, 1985, abandoned.

[30] Foreign Application Priority Data

Dec. 27, 1984 [JP] Japan .................. 59-273701
Feb. 27, 1985 [JP] Japan .................. 60-36530

[51] Int. Cl.$^4$ .................. C07C 101/32; A23L 1/236
[52] U.S. Cl. .................. 560/40; 560/41; 426/548
[58] Field of Search .................. 560/40, 41; 426/548; 548/478; 549/477

[56] References Cited

U.S. PATENT DOCUMENTS

| 3,879,372 | 4/1975 | Boesten .................. 560/40 |
| 3,933,781 | 1/1976 | Bachman et al. .................. 260/998.21 |
| 4,021,418 | 5/1977 | Takemoto et al. .................. 560/171 |
| 4,071,511 | 1/1978 | Takemoto et al. .................. 530/335 |
| 4,088,649 | 5/1978 | Smith et al. .................. 544/385 |
| 4,153,737 | 5/1979 | Berg et al. .................. 426/548 |
| 4,634,790 | 1/1987 | Shinohara et al. .................. 560/40 |

FOREIGN PATENT DOCUMENTS

| 0092933 | 11/1983 | European Pat. Off. . |
| 0127411 | 12/1984 | European Pat. Off. . |
| 2559773 | 2/1985 | France . |
| 1370 | 1/1971 | Japan . |
| 96557 | 12/1973 | Japan . |
| 113841 | 10/1976 | Japan . |
| 40069 | 11/1976 | Japan . |
| 82752 | 2/1978 | Japan . |
| 130846 | 5/1984 | Japan . |
| 225153 | 12/1984 | Japan . |
| 225152 | 12/1984 | Japan . |
| 219258 | 12/1984 | Japan . |
| 50200 | 7/1985 | Japan . |
| 174799 | 9/1985 | Japan . |
| 1359123 | 7/1974 | United Kingdom . |
| 1464140 | 2/1977 | United Kingdom . |

OTHER PUBLICATIONS

Chemical Abstracts, 105:153551s.
English-language abstract (World Patent Index) 85-244397/40.

*Primary Examiner*—John Kight
*Assistant Examiner*—Nathan M. Nutter
*Attorney, Agent, or Firm*—Fisher, Christen & Sabol

[57] ABSTRACT

This invention relates to an improved process for preparing α-L-aspartyl-L-phenylalanine methyl ester. More specifically, it relates to a process for preparing α-L-aspartyl-L-phenylalanine methyl ester which comprises treating, as a raw material, N-formyl-α-L-aspartyl-L-phenylalanine in methanol in the presence of an acid to form α-L-aspartyl-L-phenylalanine dimethyl ester, hydrolyzing the α-L-aspartyl-L-phenylalanine dimethyl ester by bringing it into contact with hydrochloric acid in the presence of methanol as desired, separating the thereby-precipitated α-L-aspartyl-L-phenylalanine methyl ester hydrochloride and neutralizing the hydrochloride. Further, this invention also provides a process for preparing α-L-aspartyl-L-phenylalanine methyl ester capable of using, as a raw material, N-formyl-α-L-aspartyl-L-phenylalanine which contains N-formyl-β-L-aspartyl-L-phenylalanine in an amount of 30% by weight or less.

9 Claims, No Drawings

PREPARATION PROCESS OF α-L-ASPARTYL-L-PHENYLALANINE METHYL ESTER

This application is a continuation of application Ser. No. 063,736, filed June 17, 1987, now abandoned.

BACKGROUND OF THE INVENTION

α-L-aspartyl-L-phenylalanine methyl ester (hereinafter abbreviated as α-APM) is a compound commonly referred to as "aspartame" and is an important substance as a sweetening agent. It has a sweetness approximately 200 times that of cane sugar and thus is in ever-increasing demand as a diet sweetening agent.

Numerous chemical preparation processes of α-APM have so far been disclosed. There may be cited a variety of processes, for example, (1) a process which comprises condensating the hydrochloride of aspartic acid anhydride and L-phenylalanine methyl ester (see, for example, Japanese Patent Publication No. 40069/1976), (2) a process which comprises condensating N-protective aspartic acid anhydride and L-phenylalanine methyl ester followed by de-protection (see, for example, Japanese Patent Laid-Open Nos. 1370/1971 and 113841/1976), (3) a process which comprises reacting N-protective aspartic acid-β- benzyl ester with L-phenylalanine methyl ester in the presence of a condensating agent followed by de-protection (see Japanese Patent Laid-Open No. 130846/1984) and (4) a process which comprises reacting N-carboxyaspartic acid anhydride and L-phenylalanine methyl ester (see Japanese Patent Laid-Open No. 96557/1973).

However, all of these processes employ L-phenylalanine methyl ester as one of the raw materials, requiring complex steps of methyl-esterification of L-phenylalanine prior to the reaction with the active derivatives of aspartic acid.

Moreover, further investigation has revealed that L-phenylalanine methyl ester is a compound in which its two free molecules in a solution are liable to condensate and cyclize to 2,5-dibenzyl-diketopiperazine and thus involves disadvantages in its stability in a solution. This fact may be responsible for various disadvantages, for example, those in the quality of α-APM, taking place in its industrial production.

Accordingly, it is desirable to develop a process which is free of these disadvantages in the production of α-APM, i.e., a process in which L-phenylalanine, not L-phenylalanine methyl ester, is used as a raw material.

As a process for preparing α-APM which does not employ L-phenylalanine methyl ester, there has been disclosed a process for preparing α-APM which comprises condensating N-formyl aspartic acid anhydride with L-phenylalanine in glacial acetic acid to form N-formyl-α-L-aspartyl-L-phenylalanine, deformylating the N-formyl-α-L-aspartyl-L-phenylalanine to form α-L-aspartyl-L-phenylalanine, and esterifying the α-L-aspartyl-L-phenylalanine to form α-APM (see Japanese Patent Publication No. 26133/1980), followed by a process in which the esterification step of the foregoing process is improved (see Japanese Patent Laid-Open No. 82752/1978).

However, since the former process brings about the esterification reaction in a substantially non-aqueous solution, the reaction has practically no freedom of selectivity so that not only the intended esterification of the α-carboxyl group of aspartic acid but also the esterification of its β-carboxyl group as well as the diesterification of its α- and β- carboxyl groups takes place to a large extent. Therefore, the process suffers such disadvantages as low selectivity and low yield of α-APM.

Further, owing to the complexity of isolating α-APM from the reaction solution after completion of the reaction, the former process is not an industrially successful process.

Given the fact that the hydrochloride of α-APM is relatively insoluble in aqueous hydrochloric acid solution, the latter process brings about the esterification of α-L-aspartyl-L-phenylalanine in the co-presence of water to deposit α-APM hydrochloride out of the reaction system. However, the yield of isolation of α-APM is at most 50–60% (based on α-L-aspartyl-L-phenylalanine) and thus is insufficient.

Further, when the reactions are effected in the same reactor in such a way that α-L-aspartyl-L-phenylalanine is first formed therein from N-formyl-α-L-aspartyl-L-phenylalanine and then esterified to produce α-APM, the deformylation reaction of N-formyl-α-L-aspartyl-L-phenylalanine must be practiced in the presence of a small amount and a low concentration of hydrochloric acid in order to suppress the cleavage of the peptide linkage.

Moreover, the subsequent esterification reaction must be carried out in a system containing small amounts of methanol, water and hydrochloric acid because the whole system has to be compact.

In this case, N-formyl-α-L-aspartyl-L-phenylalanine used as a raw material is relatively insoluble in the aqueous hydrochloric acid solution containing a small amount of methanol. Thus, such a small amount of the solvent causes the reaction mixture to form a slurry after the charge of the raw material. Therefore, various problems are liable to occur in the course of industrial operation such as in stirring.

Further, the latter process discloses that the reaction conditions have to be selected so as to suppress the formation of unfavorable α-L-aspartyl-L-phenylalanine dimethyl ester as much as possible.

Thus, the conventional processes for producing α-APM have merits and demerits in the stability of its intermediate or in reaction operation or in yield and thus are not always satisfactory.

Further, a new preparation process of α-APM in which α-L-aspartyl-L-phenylalanine dimethyl ester is hydrolyzed in an aqueous methanol-hydrochloric acid solution has lately been disclosed (see Japanese Patent laid-Open No. 219258/1984). According to this disclosure, the starting α-L-aspartyl-L-phenylalanine dimethyl ester is prepared by de-formylation and esterification of N-formyl-α-L-aspartyl L-phenylalanine methyl ester or by condensating the N-carboxylic acid anhydride of L-aspartic acid-β- methyl ester with L-phenylalanine methyl ester. Thus, the process employs L-phenylalanine methyl ester for the preparation of the starting α-L-aspartyl-L-phenylalanine dimethyl ether and therefore involves the above-described problems.

SUMMARY OF THE INVENTION

An object of the present invention is to provide a process for preparing α-APM in a more efficient manner in view of the existing state of α-APM preparation techniques as described above, and particularly to provide a process for preparing α-APM from N-formyl-α-L-aspartyl-L-phenylalanine as a raw material rather than the conventional L-phenylalanine methyl ester process which involves problems in its stability in a solution.

Another object of the present invention is to provide a process for preparing α-APM by the direct de-formylation and diesterification of N-formyl-α-L-aspartyl-L-phenylalanine followed by hydrolysis of the resulting diester.

These objects can be achieved in the following manner: first, N-formyl-α-L-aspartyl-L-phenylalanine is treated in methanol in the presence of an acid, thereby causing its de-formylation and diesterification to proceed under mild conditions so as to produce α-L-aspartyl-L-phenylalanine dimethyl ester as a primary product; then, the α-L-aspartyl-L-phenylalanine dimethylester is hydrolyzed by bringing it into contact with hydrochloric acid in the presence of methanol as desired to precipitate α-APM hydrochloride; and the thus-precipitated α-APM hydrochloride is separated and neutralized to prepare the intended α-APM in a high yield.

Moreover, in the process of the present invention, it is not always necessary to use highly purified N-formyl-α-L-aspartyl-L-phenylalanine as a raw material. It is possible to use N-formyl-α-L-aspartyl-L-phenylalanine containing its isomer N-formyl-β-L-aspartyl-L-phenylalanine without causing without causing an adverse effect upon the quality and yield of α-APM as long as the amount of the β- isomer contained therein does not exceed 30% by weight.

The process for preparing α-APM according to the present invention is beneficial in the following various respects:

(i) α-APM is prepared by way of the direct deformylation of N-formyl-α-L-aspartyl-L-phenylalanine as a raw material, followed by hydrolization after diesterification of the de-formylated product. Further, N-formyl-α-L-aspartyl-L-phenylalanine used as the raw material is prepared directly from L-phenylalanine without use of L-phenylalanine methyl ester which involves problems in its stability in a solution. As a result, the overall steps can be simplified.

(ii) Both the steps of preparing α-L-aspartyl-L-phenylalanine dimethyl ester and of preparing α-APM are both highly superior in operability and also capable of preparing α-APM of good quality in a high yield.

(iii) The N-formyl-α-L-aspartyl-L-phenylalanine used as a raw material need not be highly pure and may contain 30% by weight or less of its isomer N-formyl-β-L-aspartyl-L-phenylalanine for use as the raw material. In addition, the α-APM resulting from this material compares favorably in quality with that of the raw material of high purity, and (iv) When N-formyl-α-L-aspartyl-L-phenylalanine containing its α-isomer is used as the raw material, the β- isomer and the like other than α-APM, which can influence the production cost of α-APM, are accumulated in the filtrate after isolation of α-APM hydrochloride and can be recovered effectively as L-phenylalanine and L-aspartic acid for use as the starting materials of N-formyl-α-L-aspartyl-L-phenylalanine by subjecting the filtrate to hydrolysis, for example, through heating in a hydrochloric acid solution (L-phenylalanine and L-aspartic acid are accumulated in high concentrations in the liquid having undergone the hydrolysis so that easy concentration operation is realized after the hydrolysis, and high volume and energy efficiencies are attained in their recovery).

DETAILED DESCRIPTION OF THE INVENTION

The raw material to be used in the process of the present invention is N-formyl-α-L-aspartyl-L-phenylalanine which can be prepared by the condensation of N-formyl-L-aspartic acid anhydride and L-phenylalanine. For instance, it may be prepared by reacting N-formyl-L-aspartic acid anhydride with L-phenylalanine in glacial acetic acid at a temperature of 80° C. or below (see Japanese Patent Publication No. 26133/1980) or more efficiently by condensating N-formyl-L-aspartic acid anhydride and L-phenylalanine in a water medium under alkaline conditions followed by acidification of the resulting liquid (see Japanese Patent Application No. 264618/1984, invented by the present inventors).

In the condensation reaction as described above, the isomer, N-formyl-β- L-aspartyl-L-phenylalanine, is simultaneously by-produced in addition to N-formyl-α-L-aspartyl-L-phenylalanine. However, the N-formyl-α-L-aspartyl-L-phenylalanine used as the raw material in the process of the present invention may contain the by-produced β-isomer for use as the raw material and thus need not be of particularly high purity. In other words, N-formyl-α-L-aspartyl-L-phenylalanine containing some of its β-isomer may be used without raising any problems as a raw material in the process of the present invention as long as the content of the α-isomer does not exceed 30% by weight.

The process of the present invention comprises the step of treating the N-formyl-α-L-aspartyl-L-phenylalanine as described above in methanol in the presence of an acid to form α-L-aspartyl-L-phenylalanine dimethyl ester as a primary product and the step of hydrolyzing the α-L-aspartyl-L-phenylalanine dimethyl ester by bringing it into contact with hydrochloric acid in the presence of methanol as required to produce α-APM.

In the first step, the reaction is generally effected by charging an N-formyl-α-L-aspartyl-L-phenylalanine which contains N-formyl-α-L-aspartyl-L-phenylalanine up to 30% by weight (hereinafter, an N-formyl-α-L-aspartyl-L-phenylalanine means N-formyl-α-L-aspartyl-L-phenylalanine which contains the β-isomer in an amount of 0–30% by weight) to a methanol solution in which an acid is dissolved or by adding an acid to a solution or suspension of an N-formyl-α-L-aspartyl-L-phenylalanine in methanol.

The reaction temperature may be in the range of 10°–70° C. or preferably 20°–60° C. The reaction time varies depending on the mode or conditions of the reaction, but 0.5–50 hours or usually 1–30 hours may be sufficient for conducting the reaction.

In this manner, N-formyl-α-L-aspartyl-L-phenylalanine is de-formylated and diesterified to form α-L-aspartyl-L-phenylalanine dimethyl ester as a primary product.

In the reaction, methanol is generally used in an amount 0.2–20 times by weight that of N-formyl-α-L-aspartyl-L-phenylalanine used as the raw material, or that of the mixture of the α-isomer and the β- isomer when an N-formyl-α-L-aspartyl-L-phenylalanine is used as the raw material.

No particular problems will arise even if the amount exceeds 20 times that of the raw material. However, amounts in excess of 20 times that of the raw material are not preferred in view of the volume efficiency of the reaction vessel and the energy required for the concentration operation subsequent to the reaction. On the other hand, amounts of methanol below 0.2 times that of the raw material are not preferred from the operational viewpoint.

When the reaction is carried out using a relatively small amount of methanol, it is preferable to add intermittently or gradually an N-formyl-α-L-aspartyl-L-phenylalanine to a methanol solution in which a given amount of an acid is dissolved, from the operational viewpoint of the reaction.

As the acid useful in the first step of the process of the present invention, there may be mentioned inorganic acids such as hydrogen chloride, hydrogen bromide, sulfuric acid and phosphoric acid or organic sulfonic acids, for example, aromatic sulfonic acids such as p-toluenesulfonic acid, chlorobenzenesulfonic acid and naphthalenesulfonic acid and aliphatic sulfonic acids such as trifluoromethanesulfonic acid. Because an aqueous hydrochloric acid solution is used in the subsequent hydrolysis step, hydrogen chloride is preferred.

The amount of the acid to be used is generally 0.8–5 equivalents or preferably 1–4 equivalents relative to an N-formyl-α-L-aspartyl-L-phenylalanine to be used as the raw material.

No particular limitations are imposed on the upper limit of the amount of the acid used. However, since use of the acid in an excessive amount may cause the peptide linkage to cleave, it is preferably used in amounts of 5 equivalents or below relative to the raw material.

If the amount of the acid used is too small, the de-formylation and diesterification reactions will be incomplete.

The α-L-aspartyl-L-phenylalanine dimethyl ester formed in the above-described reactions is dissolved in methanol in the form of an acid adduct such as a hydrochloride.

Then, the second step comprises hydrolyzing the α-L-aspartyl-L-phenylalanine dimethyl ester which has been formed in the above-described reaction in the presence of hydrochloric acid, thereby forming α-APM hydrochloride. The hydrolysis is practiced by feeding an aqueous hydrochloric acid solution to the reaction solution containing the α-L-aspartyl-l-phenylalanine dimethyl ester obtained as a primary product in the first step, after the solution has been removed with the solvent methanol by distillation.

In this case, the hydrolysis reaction may be carried out either in the absence or presence of methanol by adding methanol to the hydrolysis system. When the amount of methanol used in the first step is 5 moles or less per mole of an N-formyl-α-L-aspartyl-L-phenylalanine to be used as the raw material, the hydrolysis may be conducted by feeding an aqueous hydrochloric acid solution to the reaction solution after completion of the reaction without removing methanol therefrom by distillation.

The removal of methanol from the reaction solution by distillation is effected so that the reaction solution is concentrated under reduced pressure or has an appropriate amount of water added in the course of the concentration and continuously concentrated under reduced pressure to remove the still remaining methanol.

A given amount of hydrochloric acid is added to the acid adduct of α-L-aspartyl-L-phenylalanine dimethyl ester thus-obtained, or to its aqueous solution or methanol solution, and the α-L-aspartyl-L-phenylalanine dimethyl ester is hydrolyzed by being brought into contact with hydrochloric acid to form α-APM hydrochloride.

The amount of hydrochloric acid used in the hydrolysis step is 0.5–10 moles or preferably 1–5 moles per mole of an N-formyl-α-L-aspartyl-L-phenylalanine to be used as the raw material. Further, the concentration of hydrochloric acid is so adjusted that it may be 3–30% by weight or preferably 5–25% by weight in terms of [HCl/(water +HCl)]×100, based on the remaining water in the system. The adjustment in this range will permit easy deposition of α-APM hydrochloride as a precipitate and a high yield of α-APM.

Further, as described above, the hydrolysis of α-L-aspartyl-L-phenylalanine dimethyl ester with hydrochloric acid can also be carried out in the presence of methanol. In this case, the amount of methanol present may preferably be 5 moles or less per mole of an N-formyl-α-L-aspartyl-L-phenylalanine to be used as the raw material in view of the yield of α-APM.

The temperature of the hydrolysis reaction may be 0°–50° C. or preferably 10°–40° C.. If the reaction temperature is lower than 0° C., the hydrolysis reaction will be extremely retarded and thus may take a very long time to complete, which is not favorable from the industrial standpoint. Any reaction temperatures above 50° C. will cause the solubility of α-APM hydrochloride to increase and render α-APM hydrochloride hard to precipitate, thus resulting in a lowered yield of α-APM. At the same time, disadvantageous side-reactions such as the cleavage of the peptide linkage will take place.

Although the reaction time varies depending on the reaction conditions, it is essential that sufficient time be allowed for the reaction to be completed.

In the hydrolysis reaction, α-L-aspartyl-L-phenylalanine and N-L-(α-amino-β- methoxycarbonylpropionyl)-L-phenylalanine propionyl)-L-phenylalanine and the like are by-produced in addition to the objective α-APM hydrochloride, but only α-APM hydrochloride is substantially insoluble in the reaction system and therefore precipitates out of the reaction system.

Moreover, when an N-formyl-α-L-aspartyl-L-phenylalanine, which contains N-formyl-β- L-aspartyl-L-phenylalanine, is used as the raw material, by-products derived from the β-isomer, e.g., β-L-aspartyl-L-phenylalanine, β-L-aspartyl-L-phenylalanine methyl ester, N-L-(β-amino-α-methoxycarbonylpropionyl)-L-phenylalanine and β-L-aspartyl-L-phenylalanine dimethyl ester may co-exist in the reaction solution, thus forming a complex system. However, these by-products will neither obstruct the precipitation of α-APM hydrochloride nor precipitate by themselves. Accordingly, with the passage of the reaction time, increased amounts of α-APM hydrochloride alone precipitate, leading eventually to the attainment of a high yield of α-APM.

The thus-formed α-APM precipitates out of the system as a hydrochloride. Therefore, the intended α-APM can be obtained in the following manner after completion of the hydrolysis reaction: Specifically, α-APM hydrochloride is first isolated by cooling the reaction mixture as required and subjecting it to solid-liquid separation. The resulting α-APM hydrochloride is obtained in extremely high purity without suffering deterioration of quality due to the compounds derived from the β-isomer, even when an N-formyl-α-L-aspartyl-L-phenylalanine is used as the raw material.

The α-APM hydrochloride thus-isolated is then converted to free α-APM in a conventional manner by neutralizing the hydrochloride, which is in a state of solution or suspension in water, with a base such as sodium hydroxide, sodium carbonate or sodium bicarbonate. Thus, free α-APM can be obtained in extremely high purity substantially free of impurities.

When an N-formyl-α-L-aspartyl-L-phenylalanine is used as the raw material, the β-isomer and the like other than α-APM, which can influence the production cost of α-APM, are accumulated in the filtrate which has been isolated with α-APM hydrochloride. Therefore, L-phenylalanine and L-aspartic acid can be effectively recovered for use a starting materials for N-formyl-α-L-aspartyl-L-phenylalanine by subjecting the filtrate to hydrolysis, for example, in hydrochloric acid under heating (L-phenylalanine and L-aspartic acid are accumulated in high concentrations in the solution having undergone the hydrolysis so that easy concentration operation is realized after the hydrolysis, and good volume and energy efficiencies are attained). The process of the present invention is advantageous in the above-described respects.

The present invention will hereinafter be described more specifically by the following Examples. The analytical conditions of high speed liquid chromatography employed in the Examples are as follows:
Column : YMC pack A-312 6 mmφ×150 mm (filler : ODS)
Moving phase: 0.005 M/l aqueous sodium heptanesulfonate solution : methanol =65 : 35 (volume ratio) (pH is adjusted at 2.5 with phosphoric acid)
Flow rate : 1 ml/min
Sensor : ultraviolet spectrometer

EXAMPLE 1

To a methanol solution containing 5.5 g of hydrogen chloride dissolved in 250 ml of methanol was added 30.8 g (0.1 mole) of N-formyl-α-L-aspartyl-L-phenylalanine to form a solution. The solution was subjected to reaction at room temperature for 20 hours. A portion of the reaction solution was analyzed by high speed liquid chromatography which devealed that the rate of formation of α-L-aspartyl-L-phenylalanine dimethyl ester was 100%.

The reaction solution was concentrated under reduced pressure to dryness. The residue thus-obtained was subjected to reaction at 20°-25° C. for four days by adding 16.7 g of water and 12.5 g of 35% hydrochloric acid. Thereafter, the reaction mixture was cooled to 0°-5° C. and stirred for three hours. The α-APM hydrochloride thereby-deposited was filtered and washed with cold 1N hydrochloric acid to obtain 36.2 g of a wet cake of α-APM hydrochloride. The wet cake was analyzed by high speed liquid chromatography which revealed that it contained 22.1 g of α-APM (based on free α-APM) formed in a yield of 75.2% based on N-formyl-α-L-aspartyl-L-phenylalanine.

The wet cake of α-APM hydrochloride was suspended in 220 ml of water and neutralized to a pH of 4.8 with 10% sodium hydroxide. The resulting mixture was cooled to 0°-5° C. and the deposited free α-APM was filtered. The free α-APM was then washed with cold water and dried in vacuo to obtain 20.3 g of α-APM in a yield of 69.0% based on N-formyl-α-L-aspartyl-L-phenylalanine. $(\alpha)_D^{20} = +15.9°$ (C=4, 15N formic acid).

According to an analysis by high speed liquid chromatography, no impurities were detected in the α-APM.

EXAMPLES 2-8:

Into 90 ml of methanol was dissolved 4.4 g of gaseous hydrogen chloride to form a solution to which 30.8 g (0.1 mole) of N-formyl-α-L-aspartyl-L-phenylalanine was added. The resulting mixture was subjected to reaction at 40°-45° C. for four hours. The reaction liquid was analyzed by high speed liquid chromatography which revealed that the rate of formation of α-L-aspartyl-L-phenylalanine dimethyl ester was 95%.

The reaction solution was concentrated under reduced pressure to dryness. Then, water, conc. hydrochloric acid and methanol as desired in the amounts given in Table 1 were added to the residue to hydrolyze α-L-aspartyl-L-phenylalanine dimethyl ester, therey preparing α-APM. The results are summarized in Table 1.

TABLE 1

| Ex. No. | Water (g) | Conc. hydrochloric acid (g) | Methanol (g) | Reaction temp. & time (°C./day) | Isolation yield of α-APM hydrochloride[a] (%) | Free α-APM Amount (g) | Free α-APM Yield[a] (%) |
| --- | --- | --- | --- | --- | --- | --- | --- |
| 2 | 28.7 | 20.9 | — | 30/2 | 82.1 | 22.0 | 74.8 |
| 3 | " | " | — | 20/4 | 81.8 | 21.6 | 73.5 |
| 4 | 31.3 | 41.7 | 3.2 | 30/3 | 77.8 | 21.0 | 71.5 |
| 5 | 52.3 | 20.9 | 3.2 | " | 75.3 | 20.2 | 68.7 |
| 6 | " | " | — | 20/4 | 77.5 | 20.7 | 70.4 |
| 7 | 27.9 | 20.9 | 9.6 | 30/2 | 65.3 | 17.3 | 58.7 |
| 8 | " | " | 4.8 | 20/3 | 72.3 | 19.4 | 66.1 |

Note:
[a]Yield based on N—formyl-α-L-aspartyl-L-phenylalanine

The isolation of α-APM hydrochloride was effected by cooling the reaction mixture to 0°-5° C. after completion of the reaction, filtering the solid in the mixture and washing the solid with cold 1N hydrochloric acid. The isolated α-APM hydrochloride was dissolved or suspended in water, neutralized with 20% aqueous sodium carbonate solution, cooled to 0°-5° C., filtered, washed with cold water and dried in vacuo to obtain the intended free α-APM.

EXAMPLE 9:

Into 410 ml of methanol was dissolved 27.2 g of gaseous hydrogen chloride to form a solution. To the solution was added 135 g (0.44 mole) of N-formyl-α-L-aspartyl-L-phenylalanine containing 5% of N-formyl-β-L-aspartyl-L-phenylalanine to carry out the reaction at 45°-50° C. for four hours. The reaction solution was analyzed by high speed liquid chromatography. As a result, the rate of formation of α-L-aspartyl-L-phenylalanine was found to be 95% or more.

The reaction solution was concentrated under reduced pressure until the weight of the concentrated solution was reduced to approximately 200 g. Then, 150 g of water was added thereto and the resulting solution was continuously concentrated under reduced pressure until the weight of the concentrated solution was reduced to 200 g, thereby removing the solvent methanol by distillation. To the thus-obtained solution were added 14.1 g of methanol, 44 g of water and 92.0 g of 35% hydrochloric acid and then seed crystals of α-APM hydrochloride. The reaction was effected at 30° C. for three days. Thereafter, the reaction mixture was stirred at 0°–5° C. for three hours and the α-APM hydrochloride thereby-deposited was filtered. The α-APM hydrochloride was washed with 1N hydrochloric acid which has been cooled to 5° C. or below to obtain 170.6 g of a wet cake of α-APM hydrochloride. The wet cake was subjected to high speed liquid chromatography for analysis. As a result, it was found that the wet cake contained 102 g of α-APM (based on free α-APM) formed in a yield of 83.0% based on N-formyl-α-L-aspartyl-L-phenylalanine.

The α-APM hydrochloride was suspended in 1 l of water and neutralized to a pH of 4.8 at 20°–25° C. with a 10% aqueous sodium hydroxide solution. The resulting mixture was cooled to 0°–5° C. and the solid contained therein was filtered, washed with cold water and dried in vacuo to obtain 92.5 g of free α-APM in a yield of 75.3% based on N-formyl-α-L-aspartyl-L-phenylalanine. $\alpha_D^{20} = 16.1°$ (C=4, 15N formic acid).

EXAMPLE 10

To a methanol solution containing 5.5 g of hydrogen chloride dissolved in 250 ml of methanol was added 30.8 g (0.1 mole) of a mixture consisting of N-formyl-α-L-aspartyl-L-phenylalanine and N-formyl-β-L-aspartyl-L-phenylalanine (α:β=75:25) to form a solution. The solution was subjected to reaction at 40°–45° C. for five hours. A portion of the reaction liquid was analyzed by high speed liquid chromatography. As a result, it was found that substantially all of the mixture was converted to α-L-aspartyl-L-phenylalanine dimethyl ester and β-L-aspartyl-L-phenylalanine dimethyl ester.

The reaction solution was concentrated under reduced pressure. 34 g of water and 20.8 g of conc. hydrochloric acid were added to the thus-formed syrupy residue to form a solution. The solution was subjected to reaction at room temperature for five days. Thereafter, the reaction mixture was cooled to 0°–5° C. and stirred for three hours and the thus-precipitated crystals of α-APM hydrochloride were filtered and washed with cold 1N hydrochloric acid. A wet cake of α-APM hydrochloride was obtained in an amount of 26.7 g. The wet cake was analyzed by high speed liquid chromatography which revealed that it contained 16.0 g of α-APM (based on free α-APM) formed in a yield of 72.4% based on N-formyl-α-L-aspartyl-L-phenylalanine. No compounds derived from the β-isomer were detected. The wet cake of α-APM hydrochloride was suspended in 160 ml of water and was neutralized to a pH of 5 by adding dropwise a 20% aqueous sodium carbonate solution. The resulting mixture was cooled to 0°–5° C. and the deposited free α-APM was filtered, washed with cold water and dried in vacuo to obtain 14.5 g of α-APM. $(\alpha)_D^{20} = 15.8$ (C=4, 15N formic acid)

An analysis by high speed liquid chromatography revealed no impurities in the α-APM.

EXAMPLES 11–13

In 90 ml of methanol containing 4.5 g of hydrogen chloride was reacted 30.8 g of a mixture of N-formyl-α-L-aspartyl-L-phenylalanine and N-formyl-β-L-aspartyl-L-phenylalanine (α:β=77:23) at room temperature for 24 hours to obtain a reaction mixture consisting primarily of α-L-aspartyl-L-phenylalanine dimethyl ester.

The reaction solution thus-obtained was concentrated under reduced pressure to dryness. To the residue were added hydrochloric acid in the amounts given in Table 2 so as to hydrolyze α-L-aspartyl-L-phenylalanine dimethyl ester, thereby preparing α-APM. The results are summarized in Table 2.

The isolation of α-APM hydrochloride was effected by cooling the reaction mixture to 0°–5° C. after completion of the reaction, filtering the solid in the mixture and washing the solid with cold 1N hydrochloric acid. The α-APM hydrochloride was dissolved or suspended in water, neutralized with 20% aqueous sodium carbonate solution, cooled to 0°–5° C., filtered, washed with cold water and dried in vacuo to obtain the intended free α-APM.

Both the α-APM hydrochloride and the free α-APM obtained in Examples 11–13 were found to contain no compounds derived from the β-isomer

TABLE 2

| Ex. No. | Water (g) | Conc. hydro- chloric acid (g) | Methanol (g) | Reaction temp. & time (°C./day) | Isolation yield of α-APM hydro- chloride[a] (%) | Free α-APM | |
|---|---|---|---|---|---|---|---|
| | | | | | | Amount (g) | Yield[a] (%) |
| 11 | 27.9 | 20.9 | 3.2 | 20/6 | 74.6 | 15.2 | 67.9 |
| 12 | 26.5 | 10.4 | 3.2 | 30/5 | 75.4 | 15.4 | 68.2 |
| 13 | 38.1 | 31.3 | 6.4 | 20/6 | 68.3 | 14.4 | 63.5 |

Note:
[a]Yield based on N—formyl-α-L-aspartyl-L-phenylalanine

EXAMPLE 14

Into 180 ml of methanol was dissolved 8.4 g of hydrogen chloride. To the solution was added 61.6 g (0.2 mole) of a mixture of N-formyl-α-L-aspartyl-L-phenylalanine and N-formyl-β- L-aspartyl-L-phenylalanine (α:β=77:23). The resulting mixture was subjected to reaction at 40°–45° C. for three hours.

The reaction solution was concentrated under reduced pressure until the weight of the concentrated solution was reduced to 85 g. Then, 50 g of water was added thereto and the resulting solution was continuously concentrated under reduced pressure until the weight of the concentrated solution was reduced to 80 g, thereby removing the solvent methanol by distillation. To the concentrated mixture were added 4 ml of methanol, 45 g of water and 40 g of conc. hydrochloric acid and further seed crystals of α-APM hydrochloride. Then, the reaction was carried out at 30° C. for five days. Thereafter, the reaction mixture was cooled to 0°–5° C. and stirred for three hours The thus-deposited α-APM hydrochloride was filtered and washed with cold 1N hydrochloric acid. A wet cake of α-APM hydrochloride was obtained in an amount of 59.1 g. The wet cake was analyzed by high speed liquid chromatography which revealed that it contained 34.3 g of α-APM (based on free α-APM) formed in a yield of 75.3% based on N-formyl-α-L-aspartyl-L-phenylalanine. Compounds derived from the β-isomer were not detected.

The thus-obtained wet cake was suspended in 320 ml of water and neutralized to a pH of 5 by adding dropwise a 20% aqueous sodium carbonate solution. The resulting mixture was cooled to 0°–5° C. and the deposited free α-APM was filtered, washed with cold water and dried in vacuo to obtain 31.2 g of α-APM. $(\alpha)_D^{20} = +15.7$ (C=4, 15N formic acid),

EXAMPLE 15

The reaction was carried out in the same manner as described in Example 10, except that 30.8 g of N-formyl-α-L-aspartyl-L-phenylalanine containing 10% by weight of N-formyl-β-L-aspartyl-L-phenylalanine was used. However, the temperature and time of the hydrolysis reaction were set at 30° C. and 3 days, respectively. As a result, 36.2 g of a wet cake of α-APM hydrochloride containing no compounds derived from the β-isomer was obtained. The wet cake contained 20.3 g of α-APM. The wet cake was then neutralized in the same manner in water with sodium bicarbonate to obtain 18.4 g of α-APM. As a result of an analysis by high speed liquid chromatography, no impurities were detected in the α-APM.

EXAMPLE 16

To a methanol solution containing 5.1 g of hydrogen chloride dissolved in 17.0 g of methanol was added gradually 30.8 g of N-formyl-α-L-aspartyl-L-phenylalanine at 20°–25° C. for approximately two hours. Thereafter, the reaction was effected at 45° C. for four hours. A portion of the reaction solution was analysed by high speed liquid chromatography. As a result, the rate of formation of α-L-aspartyl-L-phenylalanine dimethyl ester was found to be 70%.

Then, 29.0 g of water and 24.0 g of conc. hydrochloric acid were added to the reaction solution to carry out the reaction at 30° C. for four hours. Thereafter, the reaction mixture was cooled to 5° C. and aged at the same temperature for three hours. The thus-precipitated α-APM hydrochloride was filtered and washed with a small amount of cold water. The resulting wet cake of α-APM hydrochloride was subjected to high speed liquid chromatography for analysis. As a result, the wet cake was found to contain 23.7 g of α-APM (based on free α-APM) formed in a yield of 80% based on N-formyl-α-L-aspartyl-L-phenylalanine.

The wet cake of α-APM hydrochloride was suspended in 250 ml of water and neutralized to a pH of 5.0 with sodium hydrogen carbonate at room temperature. The resulting mixture was cooled to 0°–5° C. and the deposited free α-APM was filtered, washed with cold water and dried in vacuo to obtain 21.9 g of α-APM in a yield of 74.5% based on N-formyl-α-L-aspartyl-L-phenylalanine. $(\alpha)_D^{20} = +15.8°$ (C=4, 15N formic acid).

An analysis by high speed liquid chromatography revealed no impurities in the α-APM.

EXAMPLE b 17

To a solution containing 21.0 g of hydrogen chloride dissolved in 47.4 g of methanol was charged 117.3 g of N-formyl-α-L-aspartyl-L-phenylalanine containing 25% of N-formyl-β-L-aspartyl-L-phenylalanine at 20°–25° C. for approximately two hours. Thereafter, the reaction was effected at 40°–45° C. for four hours. A reaction mixture consisting primarily of α-L-aspartyl-L-phenylalanine dimethyl ester was obtained.

Then, 150.7 g of water and 94.1 g of conc. hydrochloric acid were added to the reaction solution to carry out the reaction at 25°–30° C. for five days. Thereafter, the reaction mixture was treated in the same manner as described in Example 16, thereby obtaining a wet cake of α-APM hydrochloride containing 61.2 g of α-APM formed in a yield of 73.0% based on N-formyl-α-L-aspartyl-L-phenylalanine. The wet cake of α-APM was neutralized in water, filtered, washed and dried in the same manner as described in Example 16 to obtain 55.1 g of α-APM in a yield of 65.8% based on N-formyl-α-L-aspartyl-L-phenylalanine. $(\alpha)_D^{20} = 15.9°$ (C=4, 15N formic acid).

What is claimed is:

1. A process for preparing α-L-aspartyl-L-phenylalanine methyl ester which comprises treating N-formyl-α-L-aspartyl-L-phenylalanine as a raw material in methanol in the presence of an acid to form α-L-aspartyl-L-phenylalanine dimethyl ester as a primary product, hydrolyzing the α-L-aspartyl-L-phenylalanine dimethyl ester by bringing it into contact with hydrochloric acid in the presence of methanol as desired, separating the thereby-deposited α-L-aspartyl-L-phenylalanine methyl ester hydrochloride and neutralizing said hydrochloride.

2. A process as claimed in claim 1 wherein the N-formyl-α-L-aspartyl-L-phenylalanine used as a raw material contains N-formyl-β-L-aspartyl-L-phenylalanine in an amount of 30% by weight or less.

3. A process as claimed in claims 1 or 2 wherein the acid is an inorganic acid.

4. A process as claimed in claims 1 or 2 wherein the acid is an organic sulfonic acid.

5. A process as claimed in claims 1 or 2 wherein the temperature of the treatment by which α-L-aspartyl-L-phenylalanine dimethyl ester is formed is 10°–70° C.

6. A process as claimed in claims 1 or 2 wherein the concentration of hydrochloric acid with which α-L-aspartyl-L-phenylalanine dimethyl ester is brought into contact is 3–30% by weight in terms of [HCl/(HCl + water)]×100.

7. A process as claimed in claims 1 or 2 wherein the amount of hydrochloric acid used is 0.5–10 moles per mole of N-formyl-α-L-aspartyl-L-phenylalanine used as a raw material, or per mole of a mixture of N-formyl-α-L-aspartyl-L-phenylalanine and N-formyl-β-L-aspartyl-L-phenylalanine when the raw material contains the β-isomer.

8. A process as claimed in claims 1 or 2 wherein the amount of methanol present as required upon hydrolyzing α-L-aspartyl-L-phenylalanine dimethyl ester by bringing it into contact with hydrochloric acid to prepare α-L-aspartyl-L-phenylalanine methyl ester hydrochloride is 5 moles or less per mole of N-formyl-α-L-aspartyl-L-phenylalanine used as a raw material, or per mole of a mixture of N-formyl-α-L-aspartyl-L-phenylalanine and N-formyl-β-L-aspartyl-L-phenylalanine when the raw material contains the β-isomer.

9. A process as claimed in claims 1 or 2 wherein the temperature at which α-L-aspartyl-L-phenylalanine dimethyl ester is brought into contact with hydrochloric acid is 0°–50° C.

* * * * *